(12) United States Patent
Takezawa et al.

(10) Patent No.: US 10,605,724 B2
(45) Date of Patent: Mar. 31, 2020

(54) MULTI-COMPONENT GAS ANALYSIS SYSTEM AND MULTI-COMPONENT GAS ANALYSIS METHOD

(71) Applicant: YOKOGAWA ELECTRIC CORPORATION, Musashino-shi, Tokyo (JP)

(72) Inventors: Shigeru Takezawa, Tokyo (JP); Takuya Yahagi, Tokyo (JP); Yoshihisa Hidaka, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 528 days.

(21) Appl. No.: 15/161,359

(22) Filed: May 23, 2016

(65) Prior Publication Data

US 2016/0349176 A1  Dec. 1, 2016

(30) Foreign Application Priority Data

May 25, 2015  (JP) ................................ 2015-105631

(51) Int. Cl.
*G01N 21/3504* (2014.01)
*G01N 21/85* (2006.01)
(Continued)

(52) U.S. Cl.
CPC .......... *G01N 21/3504* (2013.01); *G01N 9/36* (2013.01); *G01N 21/85* (2013.01);
(Continued)

(58) Field of Classification Search
CPC .......... G01N 21/3151; G01N 21/6402; G01N 21/359; G01N 21/1702; G01N 9/36;
(Continued)

(56) References Cited

U.S. PATENT DOCUMENTS 4,163,382 A * 8/1979 Amer ................. G01N 21/1702
250/351
5,127,264 A * 7/1992 Schmalz ............... G01M 9/067
73/147
(Continued)

FOREIGN PATENT DOCUMENTS

DE  19921167 A1  8/2000
JP  2000-346801 A  12/2000
(Continued)

OTHER PUBLICATIONS

Maria A. van Agthoven Near-Infrared Spectral Analysis of Gas Mixtures: pp. 593-598, vol. 56, No. 5, 2002.*
(Continued)

*Primary Examiner* — Regis J Betsch
*Assistant Examiner* — Kaleria Knox
(74) *Attorney, Agent, or Firm* — Sughrue Mion, PLLC

(57) ABSTRACT

A multi-component gas analysis system includes a spectrometric analysis device configured to obtain ratio of each of first components in a multi-component gas based on an absorption spectrum of light that has transmitted through the multi-component gas; a density measurement device configured to measure a first density of the multi-component gas; and a calculation device configured to calculate a ratio of each of second components in the multi-component gas using the ratio of each of the first components obtained by the spectrometric analysis device and the first density measured by the density measurement device, the second components being components that cannot be obtained by the spectrometric analysis device.

14 Claims, 2 Drawing Sheets

(51) Int. Cl.
*G01N 33/00* (2006.01)
*G01N 9/36* (2006.01)
*F23K 5/00* (2006.01)
*G01N 33/22* (2006.01)

(52) U.S. Cl.
CPC .......... *G01N 33/0032* (2013.01); *F23K 5/002* (2013.01); *G01N 33/0036* (2013.01); *G01N 33/0062* (2013.01); *G01N 33/225* (2013.01); *G01N 2033/0068* (2013.01); *G01N 2201/12* (2013.01)

(58) Field of Classification Search
CPC ............... G01N 21/85; G01N 21/3544; G01N 2201/12; G01M 9/067; B01D 17/0214; B01D 53/1412; C23C 14/54; F01N 33/0006; F01N 33/225; G03F 7/70033; G01G 5/0436; E21B 47/06; G02N 21/3504
USPC .......................... 250/339.13; 73/147; 702/47
See application file for complete search history.

(56) References Cited

U.S. PATENT DOCUMENTS

| | | | |
|---|---|---|---|
| 6,894,297 B1 | 5/2005 | Inoue et al. | |
| 8,574,798 B2* | 11/2013 | Iwanaga | G03G 5/0436 399/159 |
| 2004/0036023 A1* | 2/2004 | Hodgkinson | G01N 21/3151 250/339.13 |
| 2008/0288182 A1 | 11/2008 | Cline et al. | |
| 2009/0057567 A1* | 3/2009 | Bykanov | G03F 7/70033 250/429 |
| 2010/0127217 A1* | 5/2010 | Lightowlers | G01N 21/359 252/373 |
| 2012/0067219 A1* | 3/2012 | Ogawa | B01D 53/1412 95/178 |
| 2012/0253705 A1* | 10/2012 | Chen | B01D 17/0214 702/47 |
| 2013/0107244 A1* | 5/2013 | Doyle | G01N 21/6402 356/36 |
| 2014/0107943 A1* | 4/2014 | Birnkrant | G01N 33/0006 702/30 |
| 2016/0130696 A1* | 5/2016 | Price | C23C 14/54 427/10 |
| 2016/0161462 A1* | 6/2016 | Iyer | E21B 47/06 702/6 |

FOREIGN PATENT DOCUMENTS

| | | |
|---|---|---|
| JP | 2001-99781 A | 4/2001 |
| JP | 2010-530067 A | 9/2010 |
| JP | 2013-174558 A | 9/2013 |
| WO | 2008/152351 A1 | 12/2008 |

OTHER PUBLICATIONS

Jesus A. Canas, "New Downhole Fluid Analysis (DFA) TEchnologies Supporting Impoved Resservoir Managment", pp. 1-8, SPE 108097, Sep. 2007.*

* cited by examiner

MULTI-COMPONENT GAS ANALYSIS SYSTEM AND MULTI-COMPONENT GAS ANALYSIS METHOD

BACKGROUND OF THE INVENTION

Field of the Invention

The present invention relates to a multi-component gas analysis system and a multi-component gas analysis method.

Priority is claimed on Japanese Patent Application No. 2015-105631, filed on May 25, 2015, the content of which is incorporated herein by reference.

Description of Related Art

All patents, patent applications, patent publications, scientific articles, and the like, which will hereinafter be cited or identified in the present application, will hereby be incorporated by reference in their entirety in order to describe more fully the state of the art to which the present invention pertains.

In general, concentration of a specific component contained in a multi-component gas is measured using a gas chromatography. The gas chromatography includes a tubular route called a column and a gas concentration detector provided at the end of the column. The multi-component gas is transmitted thorough the column. Each of the components in the multi-component gas travels through the column at a different speed and is distinguishable (separated) thereby. The concentration of each component contained in the multi-component gas is determined by measuring the amount of each separated component with the gas concentration detector.

In addition, the concentration of the specific component contained in the multi-component gas may also be measured using a spectrometric analysis device. The spectrometric analysis device includes light source that emits light of a specific wavelength (e.g., infrared light), and a photodetector for receiving the light from the light source. In the spectrometric analysis device, the light emitted from the light source is irradiated to the multi-component gas. The light transmitted through the multi-component gas is received by the photodetector and the absorption spectrum (the spectrum of absorbance for light at each wavelength) of the received light is determined. Thereby, the concentration of each component contained in the multi-component gas is measured.

The following patent documents disclose a conventional technology that can analyze (measure) a plurality of components contained in the multi-component gas. Specifically, Japanese Unexamined Patent Application, First Publication No. 2000-346801 discloses a multi-component gas analysis method using a FT-IR (Fourier Transform Infrared) spectrometric analysis meter. Japanese Unexamined Patent Application, First Publication No. 2001-099781 discloses a gas analysis method using infrared absorption spectrophotometry. Japanese Unexamined Patent Application, First Publication No. 2013-174558 discloses a multi-component gas measurement system using a FT-IR device and an SPI-MS (Single Photon Ionization Mass Spectrometry) device.

The gas chromatograph described above can perform a measurement of concentrations for a plurality of components contained in the multi-component gas with sufficient accuracy, but it takes a long time such as about several minutes to perform the measurement. Therefore, the gas chromatograph is not suitable for the use that needs to analyze continuously the component contained in the multi-component gas (for example, a management use of a process that needs to perform an adjustment of heat quantity and an observation of components contained in a combustion gas).

On the other hand, the spectrometric analysis device described above can perform a measurement in a short time such as about several seconds. Therefore, the spectrometric analysis device can be used also for a use that needs to analyze continuously the component contained in the multi-component gas. However, the spectrometric analysis device measures the concentration of the component contained in the multi-component gas based on the absorbance of light. Therefore, the kind of components that can be measured is limited. For example, the spectrometric analysis device can measure a component that absorbs infrared light (for example, methane ($CH_4$), ethane ($C_2H_6$), or the like), while it is difficult for the spectrometric analysis device to measure a component that does not absorb infrared light (for example, diatomic molecules, such as hydrogen ($H_2$), oxygen ($O_2$), nitrogen ($N_2$), or the like).

In addition, even in a case in which the above-described component that does not absorb infrared light is contained in the multi-component gas, it is possible to measure the ratio of the component (component ratio) using the spectrometric analysis device as long as the number of the components is one. Specifically, by measuring respectively the component ratio of each component that absorbs infrared light using the spectrometric analysis device and by deducting total of these component ratios from the whole, it is possible to obtain the component ratio of the component that does not absorb infrared light. However, when a plurality of components that do not absorb infrared light are contained in the multi-component gas, it is impossible to obtain the component ratio of each of these components.

SUMMARY OF THE INVENTION

The present invention provides a multi-component gas analysis system and a multi-component gas analysis method that can continuously obtain a component ratio for each component contained in the multi-component gas even in a case in which a plurality of components that cannot be analyzed using the spectrometric analysis device are contained in the multi-component gas.

A multi-component gas analysis system according to an aspect of the present invention includes: a spectrometric analysis device configured to obtain ratio of each of first components in a multi-component gas based on an absorption spectrum of light that has transmitted through the multi-component gas; a density measurement device configured to measure a first density of the multi-component gas; and a calculation device configured to calculate a ratio of each of second components in the multi-component gas using the ratio of each of the first components obtained by the spectrometric analysis device and the first density measured by the density measurement device, the second components being components that cannot be obtained by the spectrometric analysis device.

The calculation device may be configured to calculate a second density of the multi-component gas using the ratio of each of the first components obtained by the spectrometric analysis device, and the calculation device may be configured to calculate the ratio of each of the second components by comparing the second density with the first density.

The multi-component gas analysis system may further include: a pressure measurement device configured to measure a pressure of the multi-component gas; and a temperature measurement device configured to measure a temperature of the multi-component gas. The calculation device may be configured to calculate the ratio of each of the second components using the pressure of the multi-component gas measured by the pressure measurement device and the temperature of the multi-component gas measured by the temperature measurement device, in addition to the ratio of each of the first components obtained by the spectrometric analysis device and the first density measured by the density measurement device.

The spectrometric analysis device may be a Fourier transform infrared spectrometric analysis meter, a near-infrared spectrometric analysis meter, a laser gas analysis meter, or a Raman spectrometer.

The density measurement device may be a gas densimeter or a mass flowmeter.

The first components may be components that absorb infrared light, and the second components may be components that do not absorb the infrared light.

A multi-component gas analysis method according to an aspect of the present invention may include: a first step of acquiring, by a spectrometric analysis device, ratio of each of first components in a multi-component gas based on an absorption spectrum of light that has transmitted through the multi-component gas; a second step of measuring, by a density measurement device, a first density of the multi-component gas; and a third step of calculating ratio of each of second components in the multi-component gas using the ratio of each of the first components obtained in the first step and the first density measured in the second step, the second components being components that cannot be obtained by the spectrometric analysis device.

The third step may include: calculating a second density of the multi-component gas using the ratio of each of the first components obtained in the first step, and comparing the second density with the first density.

The multi-component gas analysis method may further include: measuring a pressure of the multi-component gas; and measuring a temperature of the multi-component gas. In the third step, the ratio of each of the second components may be calculated using the pressure of the multi-component gas that has been measured and the temperature of the multi-component gas that has been measured, in addition to the ratio of each of the first components obtained in the first step and the first density measured in the second step.

The spectrometric analysis device may be a Fourier transform infrared spectrometric analysis meter, a near-infrared spectrometric analysis meter, a laser gas analysis meter, or a Raman spectrometer.

The density measurement device may be a gas densimeter or a mass flowmeter.

The first components may be components that absorb infrared light, and the second components may be components that do not absorb the infrared light.

According to each aspect of the present invention, the density measurement device that measures the density of the multi-component gas is provided in addition to the spectrometric analysis device that analyzes the component ratio of each measurable component (first component) contained in the multi-component gas. Further, the component ratio of each unmeasurable component (second component) that cannot be analyzed by the spectrometric analysis device of the components contained in the multi-component gas is obtained using the analysis result of the spectrometric analysis device and the measurement result of density measurement device. Therefore, even in a case in which a plurality of components (second components) that cannot be analyzed by the spectrometric analysis device are contained in the multi-component gas, it is possible to obtain the component ratio of each component contained in the multi-component gas continuously.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE INVENTION

The present invention will be now described herein with reference to illustrative preferred embodiments. Those skilled in the art will recognize that many alternative preferred embodiments can be accomplished using the teaching of the present invention and that the present invention is not limited to the preferred embodiments illustrated herein for explanatory purposes.

Figure 1:
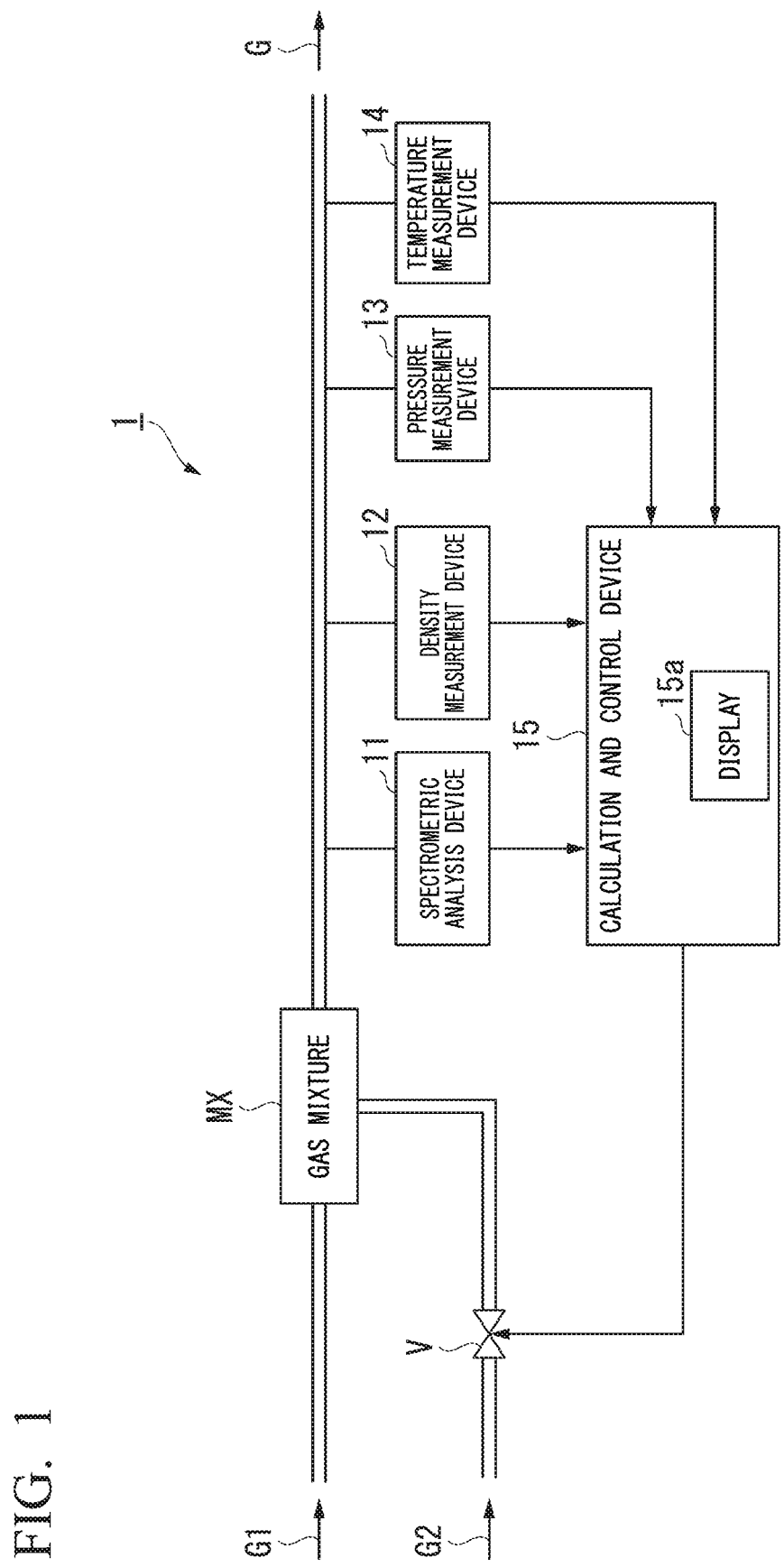
FIG. 1 is a block diagram illustrating a principal part composition of the multi-component gas analysis system in accordance with an embodiment of the present invention.

Hereinafter, a multi-component gas analysis system and a multi-component gas analysis method in accordance with an embodiment of the present invention will be described in detail with reference to the drawings. FIG. 1 is a block diagram illustrating a principal part composition of the multi-component gas analysis system in accordance with an embodiment of the present invention. As described in FIG. 1, the multi-component gas analysis system in accordance with this embodiment includes a spectrometric analysis device 11, a density measurement device 12, a pressure measurement device 13, a temperature measurement device 14, and an calculation and control device 15 (calculation device), and analyzes components contained in the multi-component gas G.

In this embodiment, to facilitate understanding, the multi-component gas G includes methane ($CH_4$), ethane ($C_2H_6$), propane ($C_3H_8$), butane ($C_4H_{10}$), pentane ($C_5H_{12}$), hydrogen ($H_2$), and nitrogen ($N_2$). Below, to facilitate description, the molecular weight of methane, ethane, propane, butane, and pentane is set to "16", "30", "44", "58", and "72", respectively, and the molecular weight of hydrogen and nitrogen is set to "2" and "14", respectively.

Here, components that absorb infrared light among the components contained in the multi-component gas are referred to as a first component, and components that do not absorb infrared light are referred to as a second component. Methane, ethane, propane, butane, and pentane are the first component. Hydrogen and nitrogen are the second component. The spectrometric analysis device can analyze the first component, while the spectrometric analysis device cannot analyze the second component.

As illustrated in FIG. 1, the multi-component gas G is obtained by a gas mixing machine MX mixing a natural gas G1 including methane, ethane, propane, butane, pentane, and nitrogen with a hydrogen gas G2. The hydrogen gas G2 is obtained by decomposing water with an electric power obtained by, for example, a wind power generation. In order to use a renewable energy effectively, the hydrogen gas G2 is used by being mixed with the natural gas G1. As illustrated in FIG. 1, the valve V for adjusting the amount of supply of the hydrogen gas G2 is provided in the supply course of the hydrogen gas G2 to the gas mixing machine MX.

The spectrometric analysis device 11 analyzes each component of methane, ethane, propane, butane, and pentane contained in the multi-component gas G based on the absorption spectrum of the light (for example, infrared light) transmitted through the multi-component gas G. The spectrometric analysis device 11 cannot analyze components such as hydrogen and nitrogen other than methane, ethane, propane, butane, and pentane contained in the multi-component gas G, because these components (hydrogen and nitrogen) do not absorb the light transmitted through the multi-component gas G. The spectrometric analysis device 11 is, for example, a laser gas analysis meter that measures each component contained in the multi-component gas G based on the absorption spectrum of the laser light that is irradiated on the multi-component gas G with laser light (for example, infrared laser light) and is transmitted through the multi-component gas G.

The density measurement device 12 measures the density (mass per unit volume) of the multi-component gas G. That is, the density measurement device 12 measures the density of the multi-component gas G containing the component (methane, ethane, propane, butane, and pentane) that can be analyzed by the spectrometric analysis device 11 and the component (hydrogen and nitrogen) that cannot be analyzed by the spectrometric analysis device 11. The density measurement device 12 is provided in order to obtain the component ratio of the component (hydrogen and nitrogen) that cannot be analyzed by the spectrometric analysis device 11. The density measurement device 12 is a gas density meter, for example.

The pressure measurement device 13 measures the pressure of the multi-component gas G. The temperature measurement device 14 measures the temperature of the multi-component gas G. The pressure measurement device 13 and the temperature measurement device 14 are provided in order to correct the density of the multi-component gas G that varies depending on the pressure and the temperature of the multi-component gas G (for example, correct the density into a value at 1 atmosphere and 0 degree C.). When the pressure and the temperature of the multi-component gas G are constant and known in advance, it is possible to omit the pressure measurement device 13 and temperature measurement device 14.

Here, the density of gas is obtained by the product of the molecularity per unit volume (the number of Mol) and the molecular weight. The molecularity n per unit volume is generally expressed as the following formula using the gaseous pressure p, the temperature (absolute temperature) T, and the gas constant R.

$$n = p/RT$$

As shown by the above formula, the molecularity n per unit volume (namely, density of gas) changes based on the gaseous pressure p and the temperature T. The pressure measurement device 13 and the temperature measurement device 14 are provided in order to correct this change.

The calculation and control device 15 obtains the component ratio of the component (hydrogen and nitrogen), which cannot be analyzed by the spectrometric analysis device 11, among the components contained in the multi-component gas G using the analysis result of the spectrometric analysis device 11 and the measurement result of the density measurement device 12. Specifically, the calculation and control device 15 compares the density of the multi-component gas G computed using the analysis result of the spectrometric analysis device 11 with the density measured by the density measurement device 12, and obtains the component ratio of hydrogen and nitrogen contained in the multi-component gas G. When the pressure measurement device 13 and the temperature measurement device 14 are provided, the calculation and control device 15 obtains the component ratio of hydrogen and nitrogen further using the measurement results of the pressure measurement device 13 and the temperature measurement device 14.

Here, a, b, c, d, and e represent the component ratio of methane, ethane, propane, butane, and pentane, which are contained in the multi-component gas G, respectively. Also, r represents the ratio of hydrogen among the component (hydrogen and nitrogen) in the multi-component gas G except methane, ethane, propane, butane, and pentane. The density ρ of the multi-component gas G is expressed by the following equation (1).

$$\rho = \rho 1 + \rho 2 \tag{1}$$

Here, ρ1 at the right side of the above equation (1) represents the density of methane, ethane, propane, butane, and pentane and is expressed by the following equation (2). Also, ρ2 of the right side of the above equation (1) represents the density of hydrogen and nitrogen and is expressed by the following equation (3). In addition, k in the following equations (2) and (3) represents a constant that is determined by the pressure and temperature of the multi-component gas G.

$$\rho 1 = k(16a + 30b + 44c + 58d + 72e) \tag{2}$$

$$\rho 2 = k((2r + 14(1-r)) \cdot (1 - (a+b+c+d+e))) \tag{3}$$

The component ratios (the variables a, b, c, d, and e in the above equations (2) and (3)) of methane, ethane, propane, butane, and pentane, which are contained in the multi-component gas G, are obtained from the analysis result of the spectrometric analysis device 11. The calculation and control device 15 compares the density ρ of the multi-component gas G, which is calculated from the above equations (1) to (3) using the analytical result of the spectroscopic analysis device 11, with the density of the multi-component gas G to be measured by the density measuring device 12, determines the ratio of hydrogen and nitrogen (variable r in the above equation (3)), and finally obtains the component ratio of hydrogen and nitrogen contained in the multicomponent gas G.

Specifically, the calculation and control device 15 obtains the component ratio of hydrogen contained in the multi-component gas G using a method described below. If the component ratio of hydrogen contained in the multi-component gas G is obtained, the component ratio of nitrogen contained in the multi-component gas G will also be obtained. First, the calculation and control device 15 obtains the component ratio f of the mixed gas of hydrogen and nitrogen contained in the multi-component gas G from the following equation (4) using the analysis result of the spectrometric analysis device 11.

$$f = 1 - (a + b + c + d + e) \tag{4}$$

Next, the calculation and control device 15 calculates the molecular weight M of the multi-component gas G from the following equations (5) and (6) using the measurement results of the density measurement device 12, the pressure measurement device 13, and the temperature measurement device 14.

$$\pi 0 = (\rho/P) \times (T/273.15) \quad (5)$$

$$M = 22.4 \times \rho 0 \quad (6)$$

Here, the above equation (5) calculates the density ρ0 of the multi-component gas G at 1 atmosphere and 0 degree C. ρ in the above equation (5) represents the density of the multi-component gas G to be measured by the density measuring device 12. P represents the pressure of the multi-component gas G to be measured by the pressure measurement device 13. T represents the temperature (absolute temperature) of the multi-component gas G to be measured by the temperature measurement device 14.

Next, the calculation and control device 15 calculates the average molecular weight Ma of the mixed gas of hydrogen and nitrogen, which are contained in the multi-component gas G, from the following equation (7) using the analysis result of the spectrometric analysis device 11, the component ratio f of the mixed gas of hydrogen and nitrogen obtained from the above equation (4), and the molecular weight M of the multi-component gas G obtained from the above equation (6).

$$Ma = (M - (16a + 30b + 44c + 58d + 72e))/f \quad (7)$$

Then, the calculation and control device 15 obtains the ratio r of hydrogen contained in the above mixed gas from the following equation (8) using the average molecular weight Ma of the mixed gas of hydrogen and nitrogen that is obtained from the above equation (7).

$$Ma = 2 \times r + 14 \times (1 - r)$$

$$r = (14 - Ma)/12 \quad (8)$$

Finally, the calculation and control device 15 obtains the component ratio f ($H_2$) of hydrogen contained in the multi-component gas G from the following equation (9) using the component ratio f of the mixed gas of hydrogen and nitrogen obtained from the above equation (4) and the ratio r of hydrogen contained in the mixed gas obtained from the above equation (8).

$$f(H_2) = f \times r \quad (9)$$

In addition, the calculation and control device 15 obtains the component ratio f ($N_2$) of nitrogen contained in the multi-component gas G from the following equation (10).

$$f(N_2) = f \times (1 - r) \quad (10)$$

Moreover, the calculation and control device 15 displays the obtained component ratio of hydrogen and nitrogen on a display 15a equipped with a display device such as a liquid crystal display device. In addition to the component ratio of hydrogen and nitrogen, the component ratio of methane, ethane, propane, butane, and pentane may be displayed on the display 15a. Also, the calculation and control device 15 controls the aperture of the valve V based on the obtained component ratio of hydrogen. For example, the calculation and control device 15 controls the aperture of the valve V so that the mixture ratio of the natural gas G1 and the hydrogen gas G2 does not become more than a predetermined ratio (for example, 15% or more).

Figure 2:
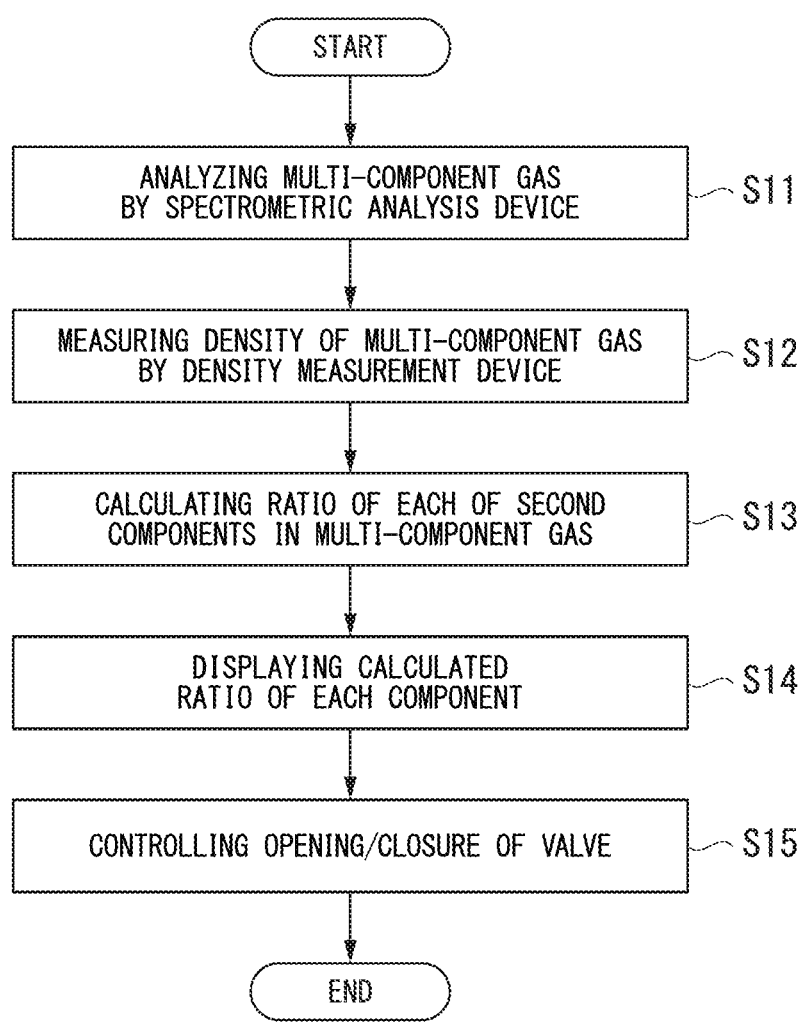
FIG. 2 is a flow chart illustrating an example of an operation of the multi-component gas analysis system in accordance with an embodiment of the present invention.

Next, operation of the multi-component gas analysis system 1 of the above-described composition will be described. FIG. 2 is a flow chart illustrating an example of operation of the multi-component gas analysis system in accordance with an embodiment of the present invention. Here, the flow chart illustrated in FIG. 2 is, for example, performed continuously or performed repeatedly with a predetermined time interval.

When processing of the flow chart illustrated in FIG. 2 is started, a process of analyzing the multi-component gas G by the spectrometric analysis device 11 is performed (Step S11, first step). Specifically, a laser light is irradiated on the multi-component gas G, the laser light transmitted through the multi-component gas G is received, an absorption spectrum is obtained, and the ratio of components (methane, ethane, propane, butane, and pentane) contained in the multi-component gas G is obtained based on the obtained absorption spectrum.

Next, a process of measuring the density of the multi-component gas G is performed by the density measurement device 12 (Step S12, second step). Here, the process of Step S12 may be performed before the process of Step S11 or may be performed in parallel with the process of Step S11. Then, a process of computing the component ratio of hydrogen and nitrogen contained in the multi-component gas G is performed by the calculation and control device 15 using the measurement results of the pressure measurement device 13 and the temperature measurement device 14 in addition to the analysis result of the spectrometric analysis device 11 and the measurement result of the density measurement device 12 (Step S13).

Specifically, first, the component ratio f of the mixed gas of hydrogen and nitrogen contained in the multi-component gas G is obtained from the above equation (4) using the analysis result of the spectrometric analysis device 11. Next, the ratio r of hydrogen of the mixed gas of hydrogen and nitrogen that is contained in the multi-component gas G is obtained from the above equations (5) to (8) using the analysis result of the spectrometric analysis device 11 and the measurement results of the density measurement device 12, the pressure measurement device 13, and the temperature measurement device 14. At the end, the component ratio f ($H_2$) of hydrogen and the component ratio f ($N_2$) of nitrogen contained in the multi-component gas G is obtained respectively from the above equations (9) and (10).

When the above processing ends, a process of displaying the computed component ratio of hydrogen and nitrogen on the display 15a is performed by the calculation and control device 15 (Step S14). Here, the component ratio of methane, ethane, propane, butane, and pentane may be displayed in addition to the component ratio of hydrogen and nitrogen. Also, a process of controlling the aperture of the valve V based on the component ratio of hydrogen computed at Step S13 is performed by the calculation and control device 15 if needed (Step S15). For example, the aperture of the valve V is controlled so that the mixture ratio of the natural gas G1 and the hydrogen gas G2 may not become more than a predetermined ratio (for example, 15% or more).

As described above, in this embodiment, in addition to the spectrometric analysis device 11 that analyzes the components contained in the multi-component gas G based on the absorption spectrum of the light transmitted through the multi-component gas G, the density measurement device 12 that measures the density of the multi-component gas G is provided. The component ratio of the component contained in the multi-component gas G is obtained using the analysis result of the spectrometric analysis device 11 and the measurement result of the density measurement device 12. Therefore, even if a plurality of components (for example, hydrogen, nitrogen, or the like) that cannot be analyzed by the spectrometric analysis device 11 are contained in the multi-component gas G, the component ratio of these components (hydrogen, nitrogen, or the like) can be measured continuously.

As described above, although the multi-component gas analysis system and the multi-component gas analysis method in accordance with an embodiment of the present invention have been described, the present invention can be freely changed within the limits of the present invention without being restricted to the above-described embodiment. For example, in the above-described embodiment, components other than methane, ethane, propane, butane, and pentane contained in the multi-component gas G were hydrogen and nitrogen. However, these components are not necessarily restricted to hydrogen and nitrogen. These components may be diatomic molecules such as oxygen ($O_2$) and chlorine ($Cl_2$) or molecules such as carbon monoxide (CO), carbon dioxide ($CO_2$), sulfur oxide (SOx), and nitrogen oxide (NOx), in addition to hydrogen and nitrogen. Namely, any of a plurality of kinds of gas may be used as long as their molecular weights differ.

Moreover, in the above-described embodiment, the laser gas analysis meter has been described as an example of the spectrometric analysis device 11. However, the spectrometric analysis device 11 is not necessarily restricted to the laser gas analysis meter. For example, FT-IR (Fourier-transform-infrared-spectroscopy) analysis meter, NIR (near-infrared) reflectance meter, or Raman spectrometer may be also used for the spectrometric analysis device 11.

Moreover, in the above-described embodiment, the gas density meter has been described as an example of the density measurement device 12. However, the density measurement device 12 is not necessarily restricted to the gas density meter. For example, mass flowmeters such as Coriolis mass flowmeter and heat type mass flowmeter may also be used for the density measurement device 12.

As used herein, the following directional terms "forward, rearward, above, downward, right, left, vertical, horizontal, below, transverse, row and column" as well as any other similar directional terms refer to those directions of an apparatus equipped with the present invention. Accordingly, these terms, as utilized to describe the present invention should be interpreted relative to an apparatus equipped with the present invention.

The term "configured" is used to describe a component, unit or part of a device includes hardware and/or software that is constructed and/or programmed to carry out the desired function.

Moreover, terms that are expressed as "means-plus function" in the claims should include any structure that can be utilized to carry out the function of that part of the present invention.

The term "unit" is used to describe a component, unit or part of a hardware and/or software that is constructed and/or programmed to carry out the desired function. Typical examples of the hardware may include, but are not limited to, a device and a circuit.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:

1. A system comprising:
    a spectrometric analysis device configured to obtain a component ratio of each first component that absorbs light and is contained in a measurement target gas based on an absorption spectrum of light transmitted through the measurement target gas;
    a density measurement device configured to measure a density of the measurement target gas; and
    a calculation device configured to calculate a component ratio of each second component that does not absorb light and is contained in the measurement target gas based on an analysis result obtained by the spectrometric analysis device and the density of the measurement target gas measured by the density measurement device,
    wherein the measurement target gas comprises one or more first components and one or more second components, whose molecular weights are already-known, and
    the component ratio is a mole ratio of the first component or the second component to a total of the first and second components contained in the measurement target gas.

2. The system according to claim 1, wherein
    the calculation device is configured to calculate a density of the first components based on the analysis result obtained by the spectrometric analysis device, and
    the calculation device is configured to calculate the component ratio by comparing the density of the first components with the density of the measurement target gas measured by the density measurement device.

3. The system according to claim 1, further comprising:
    a pressure measurement device configured to measure a pressure of the measurement target gas; and
    a temperature measurement device configured to measure a temperature of the measurement target gas, wherein
    the calculation device is configured to calculate the component ratio based on the pressure and the temperature.

4. The system according to claim 1, wherein the spectrometric analysis device is a Fourier transform infrared spectrometric analysis meter, a near-infrared spectrometric analysis meter, a laser gas analysis meter, or a Raman spectrometer.

5. The system according to claim 1, wherein the density measurement device is a gas densimeter or a mass flowmeter.

6. The system according to claim 1, wherein the light is infrared light.

7. A method comprising:
    obtaining, by a spectrometric analysis device, a component ratio of each first component that absorbs light and is contained in a measurement target gas based on an absorption spectrum of light transmitted through the measurement target gas;
    measuring, by a density measurement device, a density of the measurement target gas; and
    calculating component ratio of each second component that does not absorb light and is contained in the measurement target gas based on a result of the analyzing and the density of the measurement target gas that has been measured,
    wherein the measurement target gas comprises one or more first components and one or more second components, whose molecular weights are already-known, and
    the component ratio is a mole ratio of the first component or the second component to a total of the first and second components contained in the measurement target gas.

8. The method according to claim 7, wherein the calculating comprises:

calculating a density of the first components based on the result of the analyzing, and comparing the density of the first components with the density of the measurement target gas that has been measured.

9. The method according to claim 7, further comprising:
measuring a pressure of the measurement target gas; and
measuring a temperature of the measurement target gas,
wherein the component ratio is calculated using the pressure and the temperature.

10. The method according to claim 7, wherein the spectrometric analysis device is a Fourier transform infrared spectrometric analysis meter, a near-infrared spectrometric analysis meter, a laser gas analysis meter, or a Raman spectrometer.

11. The method according to claim 7, wherein the density measurement device is a gas densimeter or a mass flowmeter.

12. The method according to claim 7, wherein the light is infrared light.

13. The system according to claim 1, further comprising a valve,
wherein the valve is controlled based on the calculated component ratio.

14. The method according to claim 7, further comprising controlling a valve based on the calculated component ratio.

* * * * *